United States Patent
Ito et al.

(10) Patent No.: US 7,229,409 B2
(45) Date of Patent: Jun. 12, 2007

(54) METHOD OF PROVIDING A HOME HEALTH CARE SERVICE AND SYSTEM FOR PROVIDING A HOME HEALTH CARE SERVICE

(75) Inventors: Narushi Ito, Tokyo (JP); Akio Ohashi, Tokyo (JP)

(73) Assignee: NEC Corporation, Tokyo (JP)

( * ) Notice: Subject to any disclaimer, the term of this patent is extended or adjusted under 35 U.S.C. 154(b) by 503 days.

(21) Appl. No.: 10/328,222

(22) Filed: Dec. 23, 2002

(65) Prior Publication Data

US 2003/0109805 A1 Jun. 12, 2003

Related U.S. Application Data (62) Division of application No. 09/836,151, filed on Apr. 17, 2001, now Pat. No. 6,572,564.

(51) Int. Cl.
*A61B 5/05* (2006.01)
(52) U.S. Cl. .................. 600/300; 600/301; 128/920
(58) Field of Classification Search ........ 600/300–301, 600/345, 361; 702/19, 188; 705/2–4; 375/106.1–106.2; 128/903–904, 920–925; 340/573.1
See application file for complete search history.

(56) References Cited

U.S. PATENT DOCUMENTS

| 4,636,474 A | | 1/1987 | Ogura et al. | |
|---|---|---|---|---|
| 5,410,471 A | * | 4/1995 | Alyfuku et al. | 600/300 |
| 6,294,999 B1 | * | 9/2001 | Yarin et al. | 340/573.1 |
| 6,524,239 B1 | * | 2/2003 | Reed et al. | 600/300 |

FOREIGN PATENT DOCUMENTS

| EP | 0 278 631 A1 | 8/1988 |
|---|---|---|
| EP | 0 558 975 A1 | 9/1993 |
| EP | 0 682 253 A1 | 11/1995 |
| EP | 0 958 778 A1 | 11/1999 |
| JP | H01-199162 | 8/1989 |
| JP | 06-058929 | 3/1994 |
| JP | H07-074871 | 3/1995 |
| JP | H08-038435 | 2/1996 |
| JP | 08319647 A | 12/1996 |
| JP | H09-028682 | 2/1997 |

(Continued)

*Primary Examiner*—Max F. Hindenburg
*Assistant Examiner*—Michael C Astorino
(74) *Attorney, Agent, or Firm*—Scully, Scott, Murphy & Presser, P.C.

(57) ABSTRACT

A system for providing a home health care service includes a health care center, a service recipient device, and the Internet that connects these components. The health care center: is constructed on the Internet; includes a database for registering personal data that are necessary for the health care of registered at-home patients as basic health care data and storing measurement data that are provided from at-home patients over the course of time; and has the functions of inferring the health conditions of at-home patients based on the measurement data and the basic health care data, and offering appropriate services necessary for inferred health conditions. The service recipient device includes a biosensor and a signal processor. The biosensor detects chemical components contained in a substance that is discharged from the human body and converts detected values to electrical signals at the point of discharge.

21 Claims, 7 Drawing Sheets

FOREIGN PATENT DOCUMENTS

| | | |
|---|---|---|
| JP | 9-281102 | 10/1997 |
| JP | H10-074226 | 3/1998 |
| JP | 10170512 A | 6/1998 |
| JP | H10-170512 | 6/1998 |
| JP | 10-508970 | 9/1998 |
| JP | H10-248817 | 9/1998 |
| JP | H11-113859 | 4/1999 |
| JP | 11-136391 | 5/1999 |
| JP | 11-326316 | 11/1999 |
| JP | H11-312201 | 11/1999 |
| JP | 2000-2702 | 1/2000 |
| JP | 2000-88845 | 3/2000 |
| JP | 2000-102514 | 4/2000 |
| WO | WO 99/004043 | 1/1999 |

* cited by examiner

METHOD OF PROVIDING A HOME HEALTH CARE SERVICE AND SYSTEM FOR PROVIDING A HOME HEALTH CARE SERVICE

CROSS REFERENCE TO RELATED APPLICATION

The present application is a divisional of application Ser. No. 09/836,151, filed Apr. 17, 2001 now U.S. Pat. No. 6,572,564.

BACKGROUND OF THE INVENTION

1. Field of the Invention

The present invention relates to a testing device that is installed in a toilet for testing for components such as glucose, blood, protein, hormones, and vitamins that are contained in urine, and particularly to a urine glucose testing device.

The present invention further relates to a method of providing a home health care service that provides health care services to help an individual in his own home (hereinafter referred to as an "at-home patient") to manage his or her own health using the testing device; and to a system for providing a home health care service to implement this method.

2. Description of the Related Art

In the following explanation, the terms "home" or "at-home" do not necessarily mean that the individual is in his or her own home. The concept "at home" may also include cases in which the individual is in a facility that is not provided for health care, such as the company or government office where the individual is employed.

Japanese Patent Laid-open No. 319647/96 proposes a toilet-installed urine glucose inspector device that has a urine inspecting capability to sample and analyze urine by using a toilet and thus aid in an individual's health check. This device relates particularly to a sampling device for sampling urine that an individual has excreted into a toilet for urinalysis, and more specifically, to a washing mechanism of a urine collection vessel.

In this sampling device, a urine collection vessel is attached to the end of a swing arm. When sampling urine, the urine collection vessel moves by the rotation of the swing arm from a rest position that is directly below the toilet seat to a sampling position that is inside the toilet [bowl]. Urine that is collected in the urine collection vessel is conducted by way of a urine tube and urine intake tube to a urinalysis device that is outside the toilet and then tested. After sampling the urine, the urine collection vessel returns by the rotation of the swing arm to the rest position that is below the seat, where it is washed by a washing fluid that is sprayed from a nozzle.

This urine inspector device has the following defects:

The separation of the position of the urine collection vessel from the location of the device that inspects the collected urine necessitates not only piping such as a urine intake tube and a urine suction tube, but in addition, a pump for drawing up the urine to the urine inspector and solenoid valves for controlling the introduction and discharge of urine to the urine inspector.

The device is therefore large, its mechanism is complex, its potential for breakdown is high, and its maintenance costs are high. The device has additional problems in that it requires a considerable amount of time for a urine test, it uses a large quantity of chemical agents, and it must hold a large quantity of water for maintain the interior of the device clean. This example is hereinafter referred to as the first example of the prior art.

Japanese Patent Laid-open No. 170512/98 describes a toilet with a urine glucose sensor capable of easily checking for urine glucose. This example is hereinafter referred to as the second example of the prior art.

This toilet is provided with: an arm, a urine glucose sensor advancing/retracting mechanism for advancing the arm to a prescribed position in the toilet and then retracting it; and a sensor section that senses urine glucose. The sensor section is attached to the end of the arm so as to allow easy removal. After excretion of urine, the urine glucose sensor is lowered and dipped into urine in a receptacle of the toilet. The urine glucose contained in the urine in the receptacle is then checked. After use, the sensor section is subjected to washing with water, application of protective fluid, and is then retracted to a housed position. The urine glucose sensor can thus be used repeatedly.

The problem with the second example of the prior art is that when urine is discharged, the urine mixes with water that normally fills the urine receptacle. The mixture ratio of this urine and water mixture is not always fixed. For example, the same individual may sometimes pass a large quantity and at other times pass a small quantity of urine. In addition, the amount of urine discharged each time may also be influenced by temperature or the individual's age, with the result that reproducible measurement values cannot be obtained.

Furthermore, the specification describes that, in order to obtain an accurate measurement value, it is preferable to eliminate water from the receptacle by performing operations such as first flushing to rinse out the urine receptacle and additional blowing with compressed air.

As a result, the urine sensor according to the second example of the prior art is capable of only an approximate check, and various drive units or additional mechanisms are necessary if an accurate check is desired.

Explanation next concerns home health care. Conventionally, methods of managing health at home have typically involved regular recording of the measurements of instruments that can easily be procured for home use such as a thermometer, scale, sphygmomanometer [blood pressure gauge], or body fat scale and then consulting a doctor if abnormal values occur.

For diseases such as diabetes, renal disease, and liver disease in which the morbidity can be judged based on the values of chemical components of urine, urine is collected in a provided container and then inspected at a hospital or health center.

Services have also been available as health care services on the Internet in which, through the input of qualitative data of an individual's morbidity and quantitative numerical data such as height, weight, and data from periodic medical examinations, possible diseases are automatically displayed along with a doctor's comments.

However, the above-described home health care methods and Internet health care services have the following problems.

First, an at-home patient will not seek a doctor's diagnosis or give an input to the Internet regarding his or her morbidity in the absence of symptoms that he or she notices him or herself. As a result, an at-home patient may neglect to receive a doctor's diagnosis if he or she is not conscious of symptoms. Even if the at-home patient is aware of symptoms, he or she may lack the medical knowledge to judge whether the symptoms call for a doctor's diagnosis and the patient may therefore fall to receive a doctor's attention.

A second problem, relating in particular to health care for a morbidity such as diabetes that requires urinalysis, is the inconvenience of having to go to a hospital or health center to have an inspection of urine. This inconvenience originates from the impossibility of checking for urine glucose at home. Furthermore, as is well known, urine glucose varies with the passage of time after eating or with an individual's physiological condition. The patient is therefore normally required to abstain from eating for a prescribed period of time preceding a urine-test when receiving an examination at a hospital or health center. Due to this inconvenience, there has been the problem that, for morbidities that by nature require daily health care, no method has existed for health care other than yearly periodic examinations by the company or government office in which the patient is employed, or by the municipality.

The third problem is that, with regard to home health care services up to the present, it has been difficult to obtain, at home, sufficient and successive data required for health care for a morbidity. As a result, the at-home patient derives relatively little benefit relative to the difficulty entailed for input of the actual state of health of the at-home patient. There is consequently the problem that home health care services are not usually practical as a business.

It is an object of the present invention to provide a toilet-installed urine testing device that offers an improvement over the above-described first and second examples of the prior art as well as can provide easy, at-home urine testing over a period of time.

It is another object of the present invention to provide a home health care service employing the urine testing device of the present invention.

SUMMARY OF THE INVENTION

In order to achieve the above-described objects of the present invention, the urine testing device of the present invention comprising: a urine collector for collecting urine inside a toilet; a biosensor exchangeably attached inside said urine collector for detecting predetermined chemical components contained in urine to generate electrical signals; a support member for supporting said urine collector and also supporting a transmission path of said electrical signals, the support member being constructed so that urine collector may be automatically or manually moved from a housing location to a prescribed use position in the toilet bowl and vice versa; and a signal processor disposed outside the toilet for processing electrical signals supplied from the biosensor through the transmission path.

The signal processor preferably comprises an arithmetic unit that operates said electrical signals and at least one of a storage unit that stores at least one of the electrical signals and the operation results of the arithmetic unit, and a display unit that displays at least one of the electrical signals and the operation results.

The signal processor is preferably provided with a sensor calibration device.

The signal processor is preferably provided with terminals for transmitting the electrical signals and operation results of the arithmetic unit.

In this way, when the urine collector is moved to a predetermined use position to collect urine at the time of excretion, the urine is poured onto the biosensor attached inside the urine collector. The biosensor detects predetermined chemical components and generates electrical signals inside the bowl. The electrical signals is sent to the signal processor located outside the bowl through the support member.

Thus, there is no need to conduct the urine to a signal processor disposed at a location separated from the toilet bowl by pump, as with the case of the first example of the prior art.

Consequently, there is no need for components such as tubes, pumps, and solenoid valves, so that the urine testing device can be made smaller and lighter. In addition, the simplification in structure both reduces fabrication costs and decreases the potential for breakdowns caused by dirt or foam. Furthermore, since there is no need to dilute the urine, the use of chemical agents can be greatly reduced, and the costs of using the device can be decreased. Finally, the present urine testing device shortens the measurement time and therefore allows urine tests to be carried out more frequently.

Unlike the urine testing device of the second example of the prior art, the position in which urine is collected is not fixed in the present invention.

Thus, urine can be collected at any desired location without mixing of urine and water. It is to be noted that the desired location for the urine collector differs depending on, for example, sex.

In this way, the problem of the second example of the prior art can be overcome.

Next, concerning at-home health care service, the following setups are necessary in order that at-home health care service is practical as a business:

1) any at-home patient can create measurement data necessary for health care of his or her own even if the at-home patient has no special technical knowledge;
2) it is feasible to collect measurement data created by a great number of at-home patients without difficulties; and
3) it is feasible to manage centralizedly the collected data and to infer the health conditions of an at-home patient base on the measurement data and provide the at-home patient with an appropriate service for the inferred health conditions.

In order to realize the above-described setups, a first method of providing a home heath care service according to the present invention comprises steps of:

constructing a health care center on the Internet, said health care center having personal data necessary for the health care of registered at-home patients as basic health care data and also having the capability of inferring the health conditions of the at-home patients from measurement data provided by the at-home patients and said basic health care data and offering services necessary for health care or services appropriate to the inferred health conditions to said at-home patients;

distributing biosensor devices to at-home patients who wish to receive a home health care service, said biosensor device having a capability of detecting predetermined chemical components contained in a substance discharged from a human body and automatically generating electrical measurement data at the position of discharge as occasion arises;

collecting the measurement data of each registered at-home patient to said health care center from at-home patients by way of the Internet; and managing time-varying health conditions of at-home patients over a period of time based on the collected measurement data as well as said basic health care data and offering necessary services for maintaining the health of at-home patients.

Capability of the biosensor device of automatically creating the measurement data at the discharge position allows the at-home patent easily to create measurement data by a simple operation that he or she only moves the biosensor to the use position from the housing position without necessitating any technical knowledge for obtaining the measurement data.

In this way, setup 1) above can be realized.

Creating the measurement data in a form of an electric signal allows the data to be collected easily to the health care center constructed on the Internet by way of the Internet.

In this way, setup 2) above can be realized.

The measurement data collected from the at-home patients are subject to centralized management of the health care center that has a capability of providing services necessary for health care or services appropriate for the inferred health conditions to the at-home patients.

In this way, setup 3) above can be realized.

It is to be noted that the term "position of discharge" used in connection with a biosensor device means the position of the substance as it is discharged, i.e., in the case in which the substance is urine, the position of discharge refers to "inside a toilet bowl". This term is distinguished in concept from a position to which the discharged substance is guided artificially by a pipe or the like after discharge.

It is also to be noted that the detection of the discharge by the biosensor is not necessarily performed every time urine, for example, is excreted. However, because the chemical composition of an excrement from a human body ordinarily changes depending on the physiological conditions of the human body, it is desirable to detect a discharge or an excrement allowing for a time of an event that affects the physiology of a human body such as a mealtime or sleeping hours.

A system for providing a home health care service according to the present invention comprises:

a health care center constructed on the Internet and provided with a database for registering, as basic health care data, personal data necessary for the health care of registered at-home patients and for storing measurement data provided by at-home patients as occasion arises over a period of time, said health care center having a function of inferring the health conditions of the at-home patients based on said measurement data as well as said basic health care data and offering services necessary for health care or services appropriate to the inferred health conditions, to the at-home patients; and a service recipient device belonging to an at-home patient comprising: a biosensor for detecting predetermined chemical components that are contained in a substance discharged from said at-home patient and converting the detected values of the chemical components to electrical signals at the point of discharge when the discharge is conducted; a signal processor for processing an output of the biosensor and automatically generating measurement data as well as performing control of the communication between the service recipient device and the health care center; and a information terminal for interfacing the signal processor and said Internet;

wherein: the service recipient device delivers, under output control of the signal processor, measurement data that have been generated over a period of time together with time data that indicate the times when the biosensor detected the chemical component to said Internet, designating the health care center as the transmission destination; and the service recipient device receives, under input control of the signal processor, information transmitted from the health care center by way of the Internet; and wherein the health care center, when judging the transmission source of received measurement data being a service recipient device belonging to a registered at-home patient, stores the measurement data to the data base, and as demand arises, the health care center infers the health condition of the at-home patient based on stored measurement data and with reference to the registered basic health care data and offers information necessary for health care or services appropriate for the inferred health condition, to the at-home patient.

Because a biosensor automatically generates electrical measurement data of prescribed chemical components that are contained within urine, the first home health care service system of the present invention enable the collection of necessary data without requiring the at-home patient to perform any inconvenient procedures. The management of the health of a large number of at-home patients can therefore be centralized, and a home health care service can thus be organized as a business.

The substance discharged from said at-home patient can be urine excreted from the at-home patient.

In this embodiment, the biosensor, arranged inside a toilet at the time of operation, detects those measurement components among the chemical components of urine that relate to a morbidity and that change according to a daily health condition, and converts the detected values to electrical signals.

The signal processor is arranged outside of the toilet, processes electrical signals generated by said biosensor, and generates measurement data.

The health care center preferably includes an expert system for inferring the health condition of an at-home patient based on measurement data provided by the at-home patient and said basic health care data registered in a database. If the possibility of a disease of the at-home patient is inferred, the health care center searches for optimum advice for the disease through the expert system.

The health care center can have full-time specialists as staffs, or affiliated specialists who are linked to the health care center over the Internet, who are able to diagnose the health condition of the at-home patient based on measurement data provided by at-home patient and said basic health care data to provide support to the at-home patient for health care.

The health care center preferably has full-time specialists as staffs, or affiliated specialists who are linked with the health care center on the Internet, who are able to provide support to the at-home patient regarding dietary treatment, exercise therapy, or medication, as a service appropriate to an inferred health condition.

The health care center preferably affiliates with a food supplier, who is linked to the health care center on the Internet and offers food planned by the health care center to at-home patients for implementing dietary treatment appropriate for an inferred health condition.

The health care center preferably offers, as a basic service to all registered at-home patients, measurement data that have been organized and processed so as to allow easy comprehension of information relating to a specific morbidity associated with chemical components that have been measured by the biosensor. The health care center can offer, as a selective service that can be selected by at-home patients, support provided by said specialists for the specific morbidity.

As the selective service, a precise examination for a morbidity that has been inferred from measurement data can be performed at home using instructional information and materials that have been sent beforehand to an at-home patient.

The health care center preferably has a business-affiliation with a testing company having a function of testing a morbidity of at-home patients, and, as a selective service, provides the testing company with basic health care data and measurement data of an at-home patient and has the testing company perform prescribed tests of the morbidity.

The morbidity can be diabetes, and the biosensor is a sensor capable of measuring glucose, ketone bodies, hydroxybutyric acid, C peptides, or other chemical components that relate to diabetes.

The morbidity can be a liver disease, and said biosensor is a sensor capable of measuring bile acid, pyruvic acid, urobilinogen, bilirubin, or other chemical components that relate to liver diseases.

The morbidity can be a renal disease, and the biosensor is a sensor capable of measuring protein, albumin, creatinine, oxalic acid, or other chemical components that relate to renal diseases.

The biosensor can be a sensor capable of measuring lactic acid, the pH of urine, or other chemical components that serve as indicators of the degree of stress or fatigue.

The service recipient device preferably has the functions of measuring the number of times a biosensor has been used, the cumulative amount of time the biosensor has been used and a calibration value of a biosensor and sending these measurement values to said health care center as biosensor maintenance data.

In this embodiment, the health care center, as a biosensor maintenance service, stores the maintenance data in a database, notifies the at-home patient of the current biosensor state, and gives advance notice of the life of the biosensor to the at-home patient, based on the maintenance data stored in the database.

A second method of providing a home health care service is implemented in the above-described system for providing a home health care service having a capability of providing the biosensor maintenance service.

The method includes steps of:

analyzing trends in frequency of use based on the maintenance data stored in said database, deducing the time for biosensor exchange and the time that consumable supplies become necessary, delivering necessary materials before there is a lack of necessary materials, and determining monthly service charges according to the frequency of the exchange of the biosensors and the supply of the consumables, and billing the charges.

A third method of providing a home health care service by means of a health care center constructed on the Internet. The health care center has the functions of: registering, as basic health care data, personal data necessary for the health care of registered at-home patients; inferring the health conditions of at-home patients based on measurement data relating to a specific morbidity and said basic health care data, wherein said measurement data are provided by at-home patients; and offering services necessary for health care or services appropriate for inferred health conditions to at-home patients.

The third method includes steps of:

classifying said personal data and the morbidities of registered at-home patients into a plurality of categories based on measurement data, and creating lists of at-home patients belonging to each of these categories;

recruiting at-home patients who wish to communicate with each other by way of said Internet; and releasing the list of at-home patients of the same category as a recruited at-home patient to the recruited at-home patient.

A fourth method of providing a home heath care service, includes steps of:

constructing a health care center on the Internet, said health care center having personal data necessary for the health care of registered at-home patients as basic health care data and also having the capability of inferring the health conditions of the at-home patients from measurement data provided by the at-home patients and basic health care data and offering services necessary for health care or services appropriate to the inferred health conditions to said at-home patients;

distributing biosensor devices to at-home patients who wish to receive a home health care service, said biosensor device having a capability of detecting predetermined chemical components contained in a substance discharged from a human body and automatically generating electrical measurement data at the position of discharge as occasion arises;

collecting the measurement data of each registered at-home patient to said health care center from at-home patients by way of said Internet; and issuing a certificate for requesting a discount of a life insurance premium when said measurement data are within a prescribed range for at least both a predetermined period and a predetermined number of times.

The above and other objects, features, and advantages of the present invention will become apparent from the following description referring to the accompanying drawings which illustrate examples of preferred embodiments of the present invention.

DETAILED DESCRIPTION OF THE PREFERRED EMBODIMENTS

Figure 1:
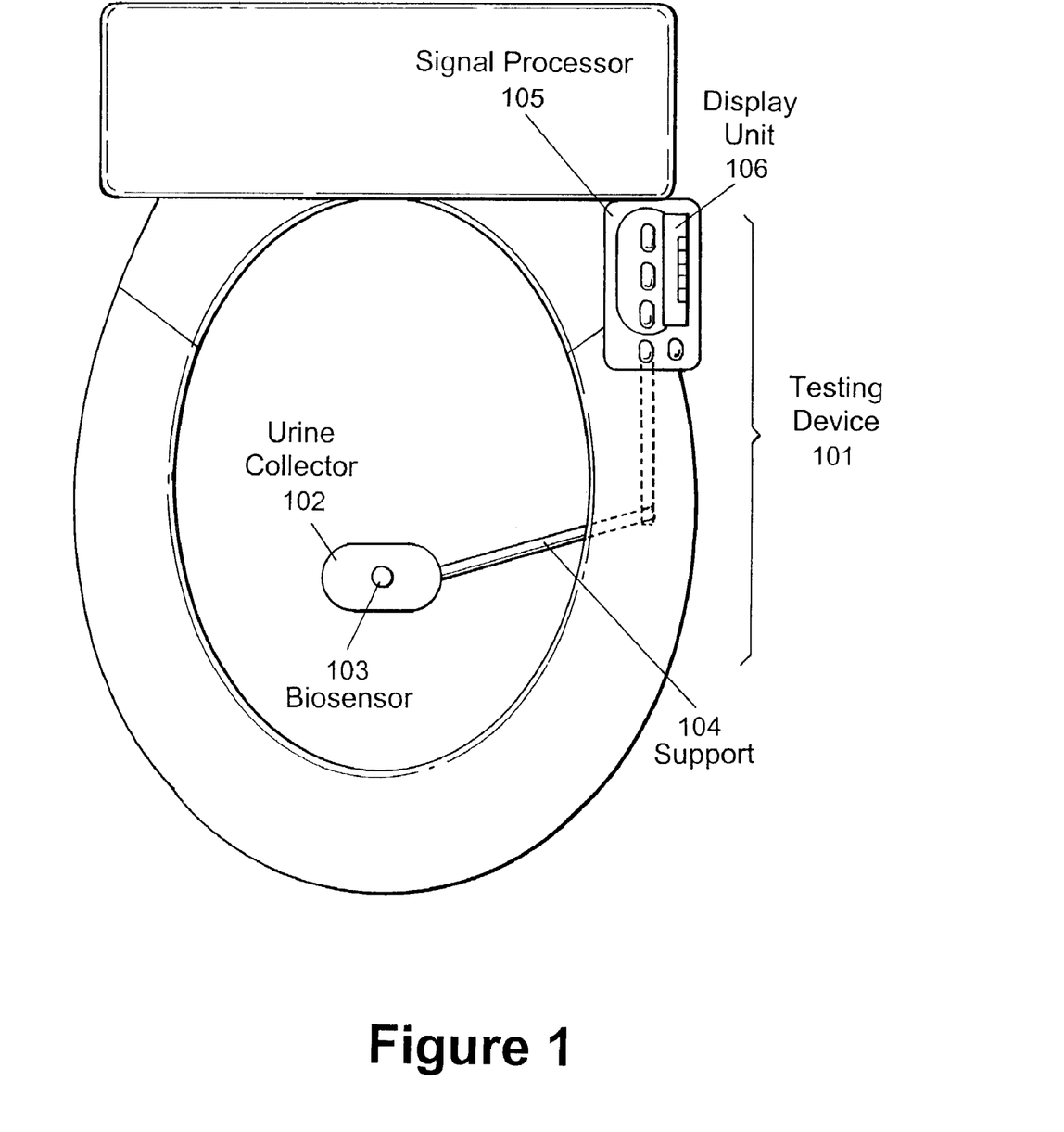
FIG. 1 is a structural view of an embodiment of the testing device used in the method of providing a home health care service of the present invention.

FIG. 1 is a structural view of an embodiment of the testing device used in the method of providing a home health care service of the present invention.

Testing device 101 is provided with: urine collector 102, biosensor 103, support 104, and signal processor 105.

Urine collector 102 is arranged in the toilet during measurement to collect urine. Biosensor 103 is arranged inside the urine collector 102, detect chemical components contained in the urine that change depending on a morbidity, and convert detected values to electrical signals. Support 104 supports urine collector 102 and also a transmission path of the electrical signals generated by biosensor 103 to signal processor 105. Signal processor 105 processes the electrical signals from biosensor 103 outside of the toilet.

Signal processor 105 is provided with: an arithmetic unit (not shown), a storage unit (not shown), and display unit 106. The arithmetic unit operates electrical signals that are generated by biosensor 103 to generate electrical measurement data. The storage unit stores the measurement data. Display unit 106 displays the electrical signals or measurement data.

Biosensor 103 of this embodiment can be exchanged according to the measurement items of the morbidity to be examined. In the present embodiment, a biosensor is provided having the capability of the effecting the following measurements according to each of various morbidities.

Morbidity: Diabetes
Measurement items: Glucose, ketone bodies, hydroxybutyric acid, C peptide, and other chemical substances that change according to the diabetic state.

Morbidity: Renal Disease
Measurement items: Protein, albumin, creatinine, oxalic acid, and other chemical substances that change according to the state of a renal disease.

Morbidity: Liver Disease
Measurement items: bile acid, pyruvic acid, urobilinogen, bilirubin, and other chemical substances that change according to the state of a liver disease.

In addition, the measurement items may include: lactic acid, which changes according to the amount of exercise; and pH, which changes according to diet.

Testing device 101 is also capable of calibration as will be described with reference to FIG. 3.

When a user is to use this testing device, urine collector 102 is automatically or manually moved from a housing location to a prescribed position (a use position) in the toilet bowl. Urine that collects in urine collector 102 is analyzed by biosensor 103 arranged in urine collector 102. Electrical signals from biosensor 103 are processed by signal processor 105, and the results of this processing are displayed on display unit 106. This signal processor 105 may be provided as a single unit with biosensor 103 and urine collector 102. In addition, the results of computation by signal processor 105 are stored in the storage unit.

Figure 2:
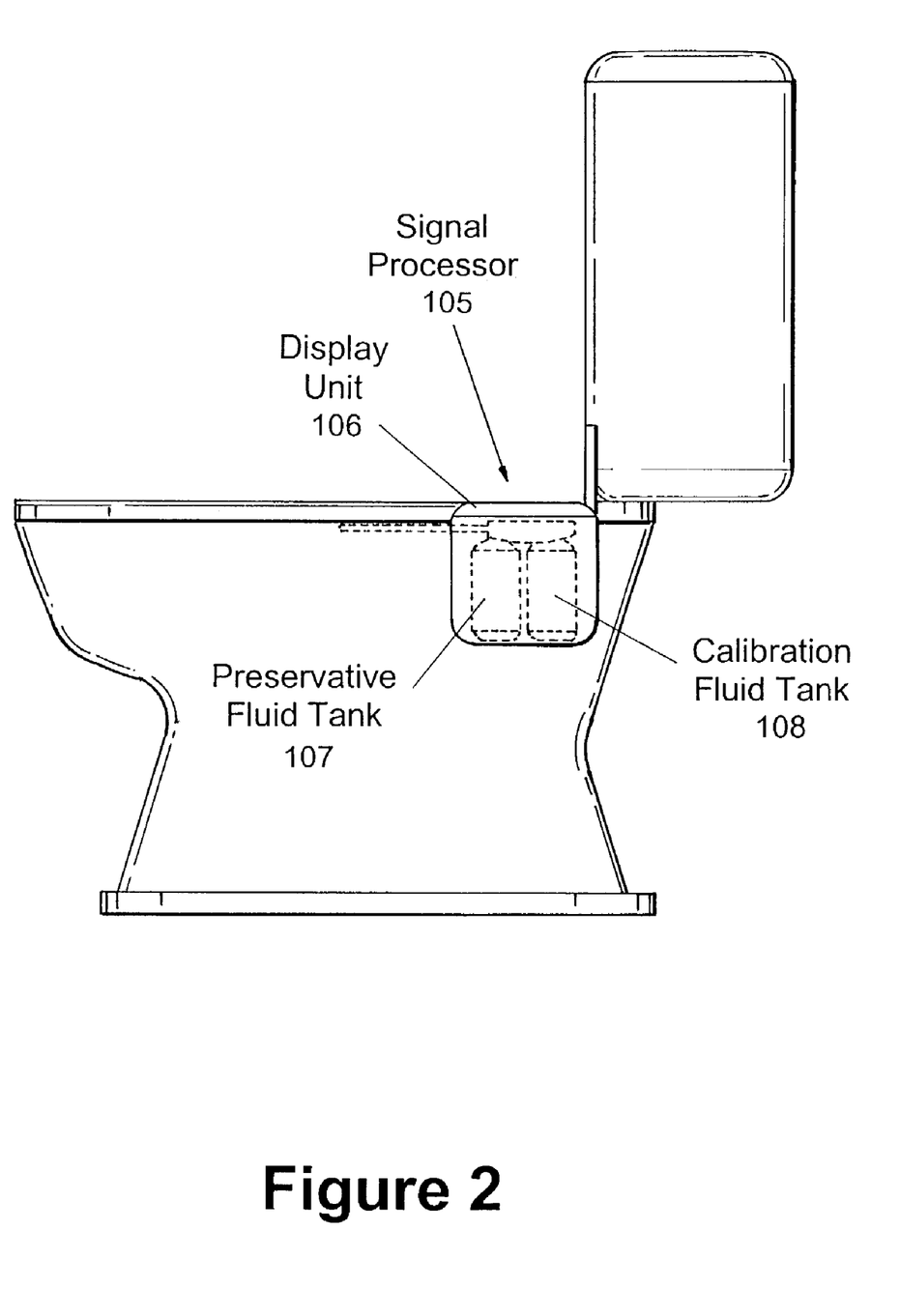
FIG. 2 shows a side view of signal processor of the testing device shown in FIG. 1.

FIG. 2 shows a side view of signal processor 105. Display unit 106 is arranged on the top of signal processor 105, and preservative fluid tank 107 and calibration fluid tank 108 are received under display unit 106. Urine collector 102, after measurement of urine or calibration fluid finishes, is normally filled with preservative fluid so that the preservative fluid may contact biosensor 103 to serve for preserving the performance of biosensor 103 over an extended time period. The preservative fluid contains salts of a prescribed concentration, a buffer for maintaining pH at a constant value and an antiseptic for preventing multiplication of bacilli. The calibration fluid is made up of the above-described preservative fluid and a substance to be tested of a predetermined concentration.

Figure 3:
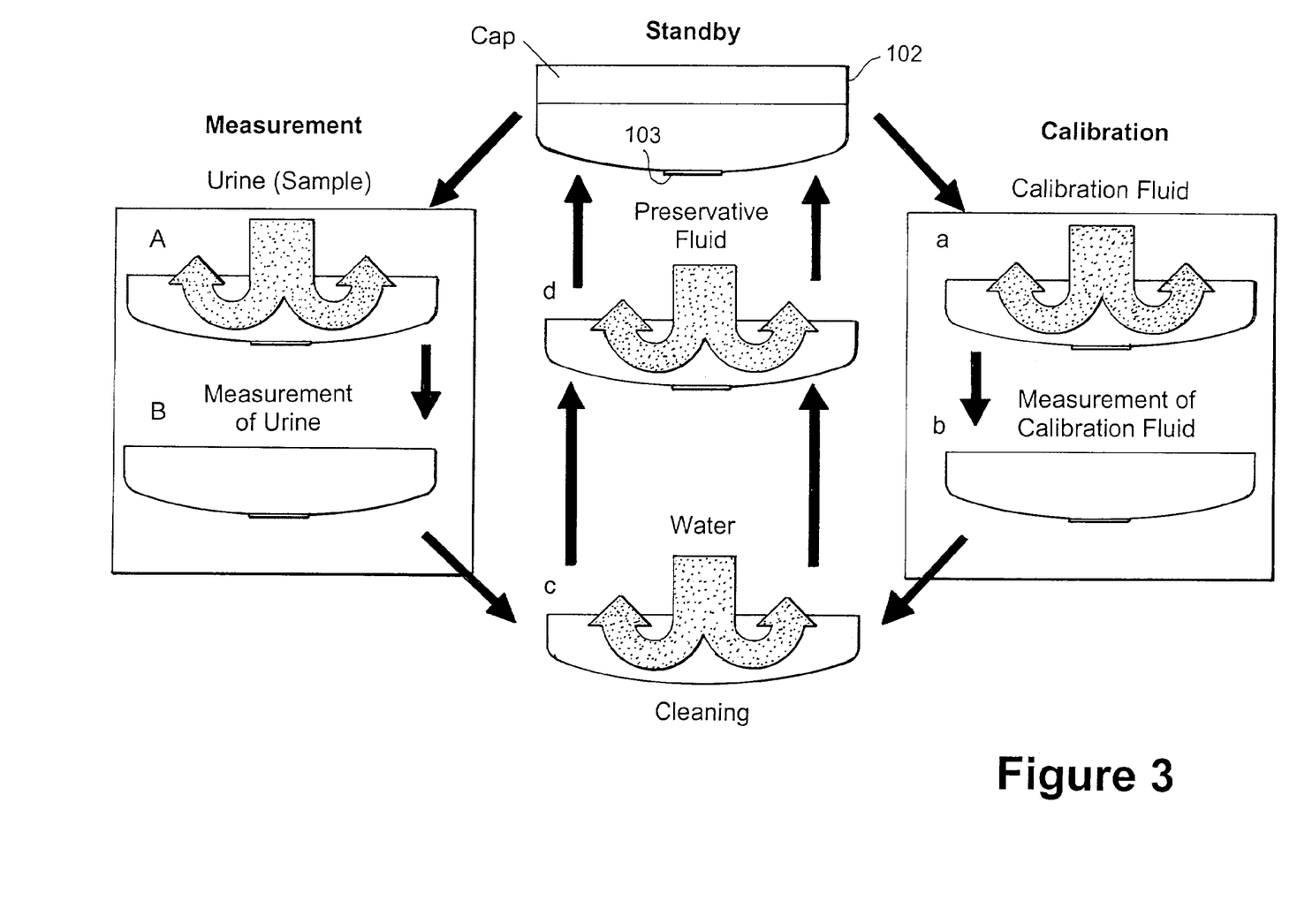
FIG. 3 shows the procedures of urine-glucose measurement and calibration.

FIG. 3 shows the procedures of urine-glucose measurement and calibration. When measuring urine glucose (as depicted on the left section of the figure), urine collector 102 moves to a predetermined use position, where urine is replaced for preservative fluid (step A); urine glucose is then sensed (step B); urine collector 102 is moved back to the original housing position, where the inside thereof is cleaned with water (step c); water in urine collector 102 is replaced with preservative fluid (step d); and finally, urine collector 102 is capped to prevent biosensor 103 from drying-up caused by evaporation of the preservative fluid, and then put in the standby state.

When calibration of the urine testing device is implemented (as depicted on the right section of the figure), urine collector 102 moves to a predetermined position, where calibration fluid is replaced for preservative fluid (step a); the calibration fluid is tested (step b); urine collector 102 is moved back to the original housing position, where the inside thereof is cleaned with water (step c); water in urine collector 102 is replaced with preservative fluid (step d); and finally, urine collector 102 is capped to prevent biosensor 103 from drying-up caused by evaporation of the preservative fluid and then put in the standby state.

It is possible to use preservative fluid in lieu of water. In this case, the number of steps is fewer. Moreover, a simple pump can be employed for pouring the preservative fluid or calibration fluid into the urine collector. The reason for this is that, while a volume of the fluid is required to be over a predetermined value, the value is small enough as compared to the performance of a simple pump. Furthermore, since the urine collector is small in volume, the replacing fluid can be of a small quantity.

Figure 4:
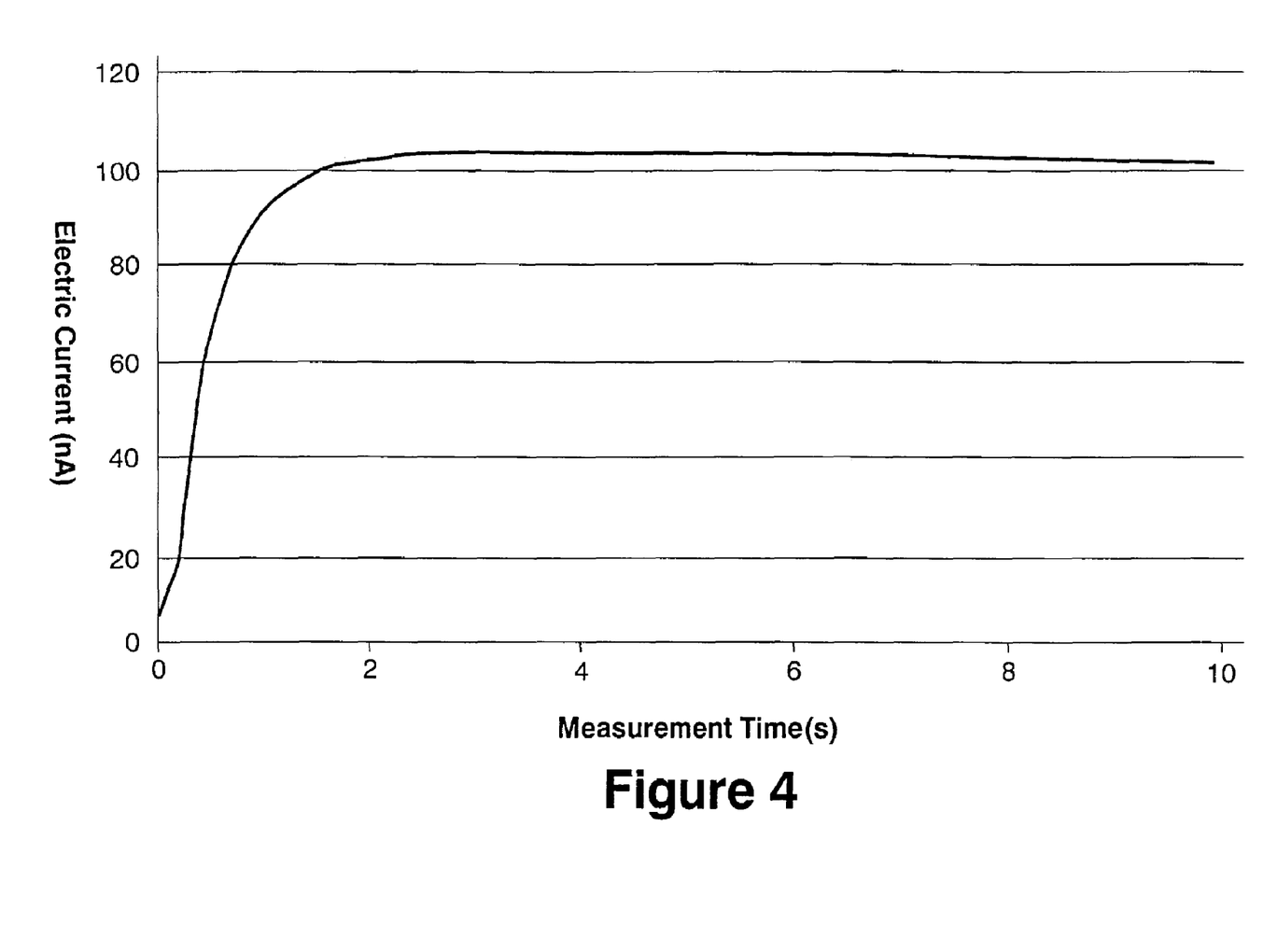
FIG. 4 represents a time dependent response characteristic of the electric current provided as an output of a biosensor.

FIG. 4 represents a time dependent response characteristic of the electric current provided as an output of a biosensor when glucose in urine is detected. It is seen that the current reaches a saturated value in 3 seconds after a start of measurement (time 0). The increment of the saturated current value minus the start-time current value depends on the concentration of urine glucose. An accurate concentration of urine glucose in urine can be computed by computing the reference glucose concentration based on the output of the biosensor immersed in the calibration fluid of a known glucose concentration.

When using the testing device, a database indicating the health condition of each individual can be constructed by entering the name or ID number of the user as input to signal processor 105.

It is further possible to record the time of urine collection by incorporating a timer in signal processor 105.

A wide variety of data can also be integrated if signal processor 105 is provided with input terminals for the data of a portable biosensor.

A statistics-processing unit for performing statistical processing of the above-described database may also be incorporated into signal processor 105. Transmitting a database or data that have undergone statistical processing to a medical institution by way of a communications line enables diagnosis of the health condition of a user remaining at home.

It is also possible to control diet based on these databases.

Sending these data by way of a data line to, for example, a home meal delivery service enables the menu of meals for each day to be sent by way of the data line. It is also possible to home-deliver meals based on these menus.

These menus may be prepared based on instructions from a medical facility.

Since two-way communication with the medical facility is possible, the results of diagnosis can also be stored in the storage unit. A medical prescription may also be added to the results of diagnosis.

In addition, a health condition history or the result of a diagnosis that is saved in the storage unit can be used as a basis for calculating a life insurance premium or for various services according to an individual's health condition.

Figure 5:
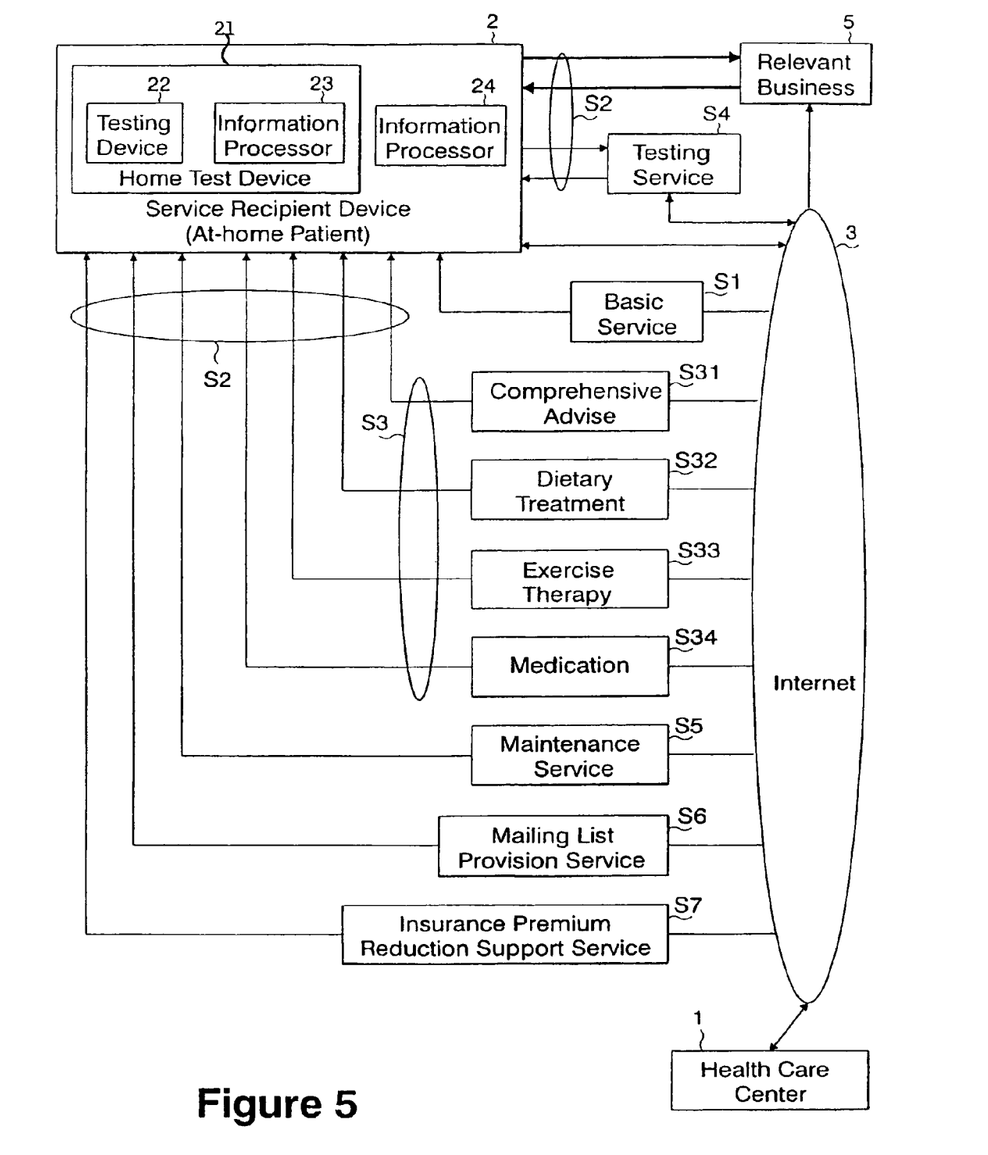
FIG. 5 is a block diagram showing an embodiment of the system for providing a home health care service.

FIG. 5 is a block diagram of an embodiment of a system for providing a home health care service that implements the method of providing a home health care service of the present invention.

In the system for providing the home health care service of this embodiment, health care center 1, which is the service provider, is connected via the Internet 3 to service recipient (at-home patient) device 2.

Health care center 1 is provided with a database (not shown in the figure) and a diagnostic expert system (not shown). Personal data that are necessary for the health care of registered at-home patients are recorded as basic health care data in the database, and measurement data that are provided from at-home patients over the course of time are stored in the database.

The expert system infers the health condition of an at-home patient based on the measurement data provided from the at-home patient as well as the personal data stored in the database. If the system infers the possibility of a morbidity in an at-home patient, searches for the best advice for that morbidity, and further, searches for services that are necessary for health care or for services that are appropriate to the inferred health condition.

Health care center 1 has full-time specialists as staffs or has affiliated specialists who are linked over the Internet. These specialists are able to diagnose the health condition of the at-home patient and give the at-home patient the necessary support, based on measurement data provided by the at-home patient and with reference to the basic health care data. In addition, health care center 1 has full-time specialists as staffs, or has affiliated specialists linked over the Internet, who can provide the at-home patient with support regarding dietary treatment, exercise therapy, or medication as a service appropriate to an inferred health condition.

Food providers who offer foods planned by the health care center to provide a dietary treatment appropriate to a inferred health condition are also affiliated with health care center 1.

At-home patient (service recipient device) 2 is provided with home testing device 21 and information terminal 24; and home testing device 21 is provided with testing device 22 and information processor 23. Testing device 22 has the same construction as testing device 101 of FIG. 1 and detects, at home and over the course of time, predetermined chemical components contained in a substance discharged from the human body, and automatically converts the detected values to electrical measurement data. Meaurements of the chemical components change depending of morbidity.

Information processor 23 processes the output of testing device 22, automatically generates measurement data in a prescribed format. Information processor 23, moreover, performs both output control and input control. The output control is intended for sending measurement data together with time data to health care center 1 by way of Internet 3. The time data indicate the times in which the measurement data were obtained. Input control is intended for receiving information (service) sent from health care center 1 by way of Internet 3. Information terminal 24 interfaces between information processor 23 and Internet 3. Information terminal 24 may include a dedicated terminal, a set-top box that is connected to a TV, a personal computer, a portable telephone, or a facsimile.

Home testing device 21 sends measurement data that have been generated over a period of time to Internet 3 by way of information terminal 24 designating health care center 1 as the transmission destination. Health care center 1, when receiving measurement data and judging the received measurement data as transmitted from a registered at-home patient (service recipient device) 2, stores the measurement data into the database. Health care center 1 enters the measurement data and the basic health care data into the expert system as occasion demands and infers the health condition of at-home patient 2 in accordance with the output of the expert system.

Health care center 1 thus provides the at-home patient with information required for health care or with service appropriate to the diagnosed health condition in accordance with the diagnosis of a staff specialist or an affiliated specialist (usually a physician), or the output of the expert system.

In this embodiment, the service that health care center 1 provides to at-home patient 2 includes basic service S1 and selective services S2.

Basic service S1 is a service that health care center 1 provides to all registered at-home patients; and selective services S2 are services that an at-home patient can select.

The services provided by health care center 1 will next be described with regard to a working example in which a urine glucose biosensor is employed as testing device 22.

In this working example, health care center 1 offers, as basic service S1, a service in which the urine glucose values are totalized and visualized to enable easy extraction of information on diabetes in relation to urine glucose that has been measured by biosensor 22. Based on the totalization of the measurement data, health care center 1 provides at-home patient (service recipient device) 2 by way of the Internet with graphs (visualizations) of past measurement values, average values, and trends in the change of urine glucose values on a measurement-time basis. Preparing visualizations of the measurement values in this way helps the at-home patient understand his or her own health condition. Data obtained by this process are also registered in the database. With regard to such a morbidity of an at-home patient as requires no diagnosis of a specialist, health care center 1 notifies, as basic service S1, any judgments relating to his or her health care, as comments, to him or her. Health care center 1 also provides education to the at-home patient regarding diabetes.

As the selective services, health care center 1 provides the at-home patient with support given by specialists for specific morbidity.

In this working example, selective service S2 includes advice service S3 by specialists, testing service S4, and maintenance service S5. In addition, mailing list provision service S6 and insurance premium reduction support service S7 are also included as special services.

Specialist advice service S3 further includes: comprehensive advice service S31, dietary treatment support service S32, exercise therapy support service S33, and medication support service S34.

Comprehensive advice service S31 is a service for preparing comprehensive advice for diabetes by specialists (chiefly physicians) based on the measurement data that have been collected by health care center 1 and providing at-home patients 2 with this advice by way of the Internet.

In this way, the exact judgment (advice) of a physician can be easily obtained at home based on the most recent measurement data.

Dietary treatment support service 32 provides, over the Internet, at least one meal menu that is optimum for the user (taking into consideration such factors as calories, nutritional balance, and the user's preferences). The meal menu can be created based on dietary items of the at-home patient derived from data collected at the center, as well as on the opinions of specialists such as doctors and dieticians. Such dietary items can be, for example, the meal times, meal content, past measurement values, average values, and trends of change in urine glucose values plotted on a measurement-time basis.

In addition, if a home delivery service is selected, meals or food stuff for preparing the above-described meal menu can be delivered to the home by a food supplier (relevant business 5).

By thus combining urine glucose data and other data, the optimum meal menu can be drawn up in real time (as circumstances dictate). As an example, an additional dish might be added to a patient's diet when the patient's condition continues to improve for two or three days.

Exercise therapy support service S33 determines, through the medium of an exercise therapist or sports instructor, an appropriate exercise regimen based on exercise items of an at-home patient that have been derived from data collected at the center.

The exercise items can be, for example, exercise information, past measurement values, average values, and trends of change in urine glucose values plotted on a measurement-time basis.

Exercise therapy support service S33 then provides this information to the at-home patient by way of the Internet. Exercise therapy support service S33, in addition, can recommend appropriate exercise equipment The effect of an exercise therapy can be improved by thus obtaining an accurate understanding of the relation between urine glucose data and the amount of exercise.

Medication support service S34 determines, through the medium of a physician or pharmacist, the sort and dosage of medication in real time based on medication items and other information regarding the at-home patient that has been extracted from data collected at the center. The medication items can be the medications used by the at-home patient, past measurement values, average values, trends of variations in urine glucose values plotted on a measurement time basis. Medication support service S34 provides this medication information to the at-home patient by way of the Internet.

The proper sort and dosage of medication can be easily determined using real-time urine glucose data, and the effect of home health care can be improved.

Testing service S4 is a service for examining a diabetic condition (glucose tolerance condition). In this examination, a precise test of the morbidity is carried out at home using instructional information and materials that have been sent in advance. In this embodiment, the at-home patient is administered an oral glucose tolerance test (a test in which the urine glucose level is measured after the passage of a fixed time after drinking a glucose solution on an empty stomach) at home. Detailed information of a patient's condition or other biochemical information is collected from the at-home patient by way of the Internet in order to obtain further information regarding the morbidity of the at-home patient. This information is compared with other data of the at-home patient that have been registered in the database as well as with past information of the at-home patient accumulated at health care center 1 to realize a highly reliable examination. Thus, a self-employed worker or a homemaker who ordinarily has few opportunities to have a medical examination can easily undergo an examination for diabetes. In addition, an oral glucose tolerance test has a higher potential for early discovery of abnormal glucose tolerance than an ordinary examination (a urine test performed when the patient has not eaten), and the oral glucose tolerance test is effective for an individual who habitually receives examinations as well.

Regarding the arrows between testing service S4 and at-home patient 2 in FIG. 5, the arrow directed from testing service S4 to at-home patient 2 represents instructional information for the oral glucose tolerance test from health care center 1 to at-home patient 2 for the testing service, wherein the instructional information is sent directly by telephone or facsimile. The arrow directed from at-home patient 2 toward testing service S4 represents questions etc. that health care center 1 receives from at-home patients directly by telephone or facsimile. The glucose to be used in the oral glucose tolerance test is provided to at-home patient 2 by relevant business 5 in accordance with the instructions of health care center 1.

Maintenance service S5 is a service for supporting the maintenance of the urine glucose biosensor.

The cumulative time that a biosensor has been used and the cumulative number of times of use of the sensor are measured with each use of the biosensor by a timer and counter that are incorporated in the urine glucose biosensor, and are sent to health care center 1 together with the measurement data. By means of this maintenance service S5, the life of the biosensor and the amount of spent consumable supplies are judged based on the data that have been comprehensively combined at health care center 1. At-home patient 2 is notified by way of the Internet regarding the state or remaining usefulness of biosensor 22. In addition, exchangeable components or consumable supplies can be supplied from the urine glucose biosensor manufacturer (relevant business) 5 by means of a home delivery service.

Health care center 1 can thus provide maintenance of a home testing device without need for a business to visit the at-home patient. In addition, parts can be exchanged at the proper timing.

In FIG. 5, the heavy arrows between relevant business 5 and at-home patient 2 represent the movement of articles. In most cases, these articles flow from relevant business 5 to at-home patient 2, but in a case in which relevant business 5 checks components of home testing device 21, for example, the articles flow from the home testing device 21 to relevant business 5.

As other selective services S2, health care center 1 also provides morbidity-specific mailing list service S6 and insurance premium reduction support service S7. Although these services are not directly related to medical treatment, they improve a sense of the health care of at-home patient 2.

Morbidity-specific mailing list service S6 is a service for creating a mailing list based on the age and sex of the patients and the urine glucose values that have been collected by way of Internet 3. Health care center 1 recruits at-home patients who wish to communicate with other registered at-home patients by way of the Internet, and provides an enlisted at-home patient with a name list of the enlisted home patients having the same morbidity. The at-home patient, if wishes, may communicate information (relating current condition, giving advice, competing, etc.) within the mailing list.

This allows each group (mailing lists) of at-home patients of similar age having similar morbidity to share similar hardships regarding diabetes. This can be useful for encouraging the at-home patients.

Insurance premium reduction support service S7 is a service providing resources for reducing insurance premiums for the next and following years based on urine glucose levels and number of measurements that have been collected by way of the Internet during a particular period (for example, one year).

Thus, in a case in which periodic measurements are taken, a service is made possible that issues a certificate for discounting the next year's insurance premium when the progression of a morbidity cannot be observed from urine glucose levels.

Figure 6:
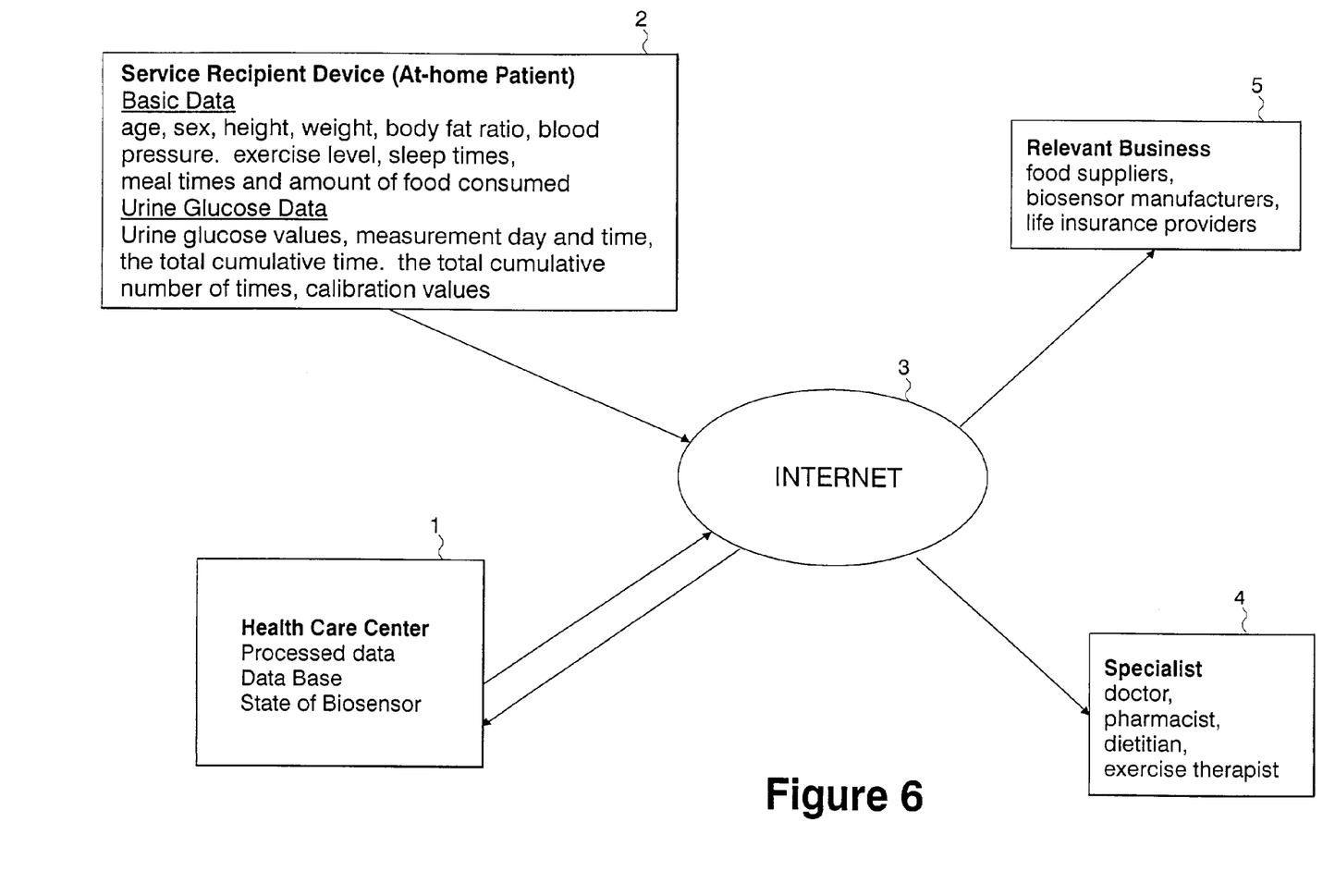
FIG. 6 is a block diagram showing the flow of data of the system for providing the home health care service of FIG. 5.
Figure 7:
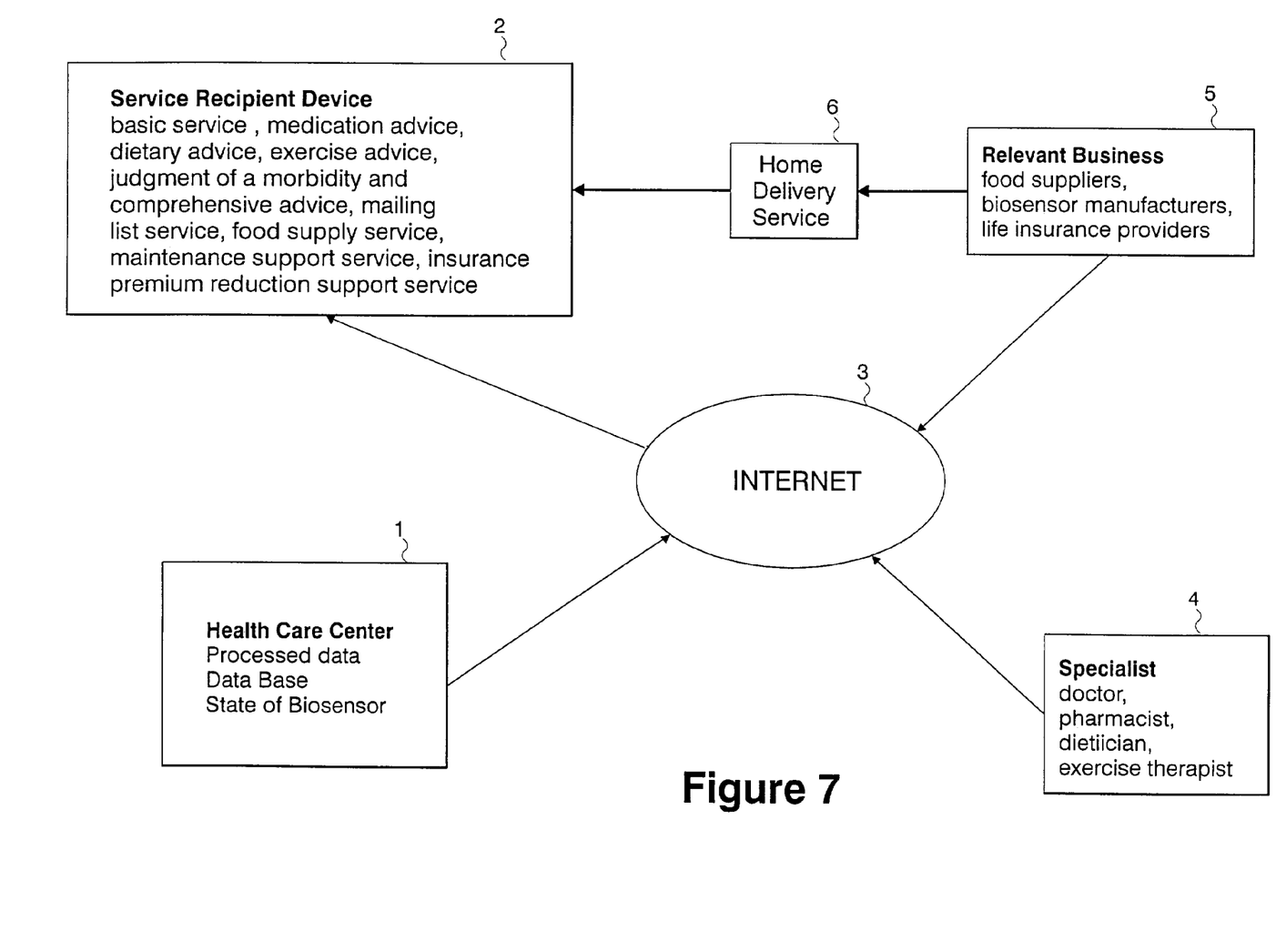
FIG. 7 is a block diagram showing the flow of the service of the embodiment of FIG. 6.

FIG. 6 is a block diagram showing the flow of data in an embodiment of the system for providing a home health care service that implements the method of providing a home health care service of the present invention. FIG. 7 is a block diagram showing the flow of services of the embodiment of the system for providing a home health care service shown in FIG. 6.

Referring now to FIG. 6, all data flow from at-home patient 2 and are gathered at health care center 1, following which necessary data flow to specialists 4 and relevant businesses 5.

At-home patient (the user of a urine glucose biosensor) 2 transmits basic health care data (hereinbelow referred to as "basic data") and urine glucose data to the Internet designating health care center 1 as the destination.

Basic data are registered into the database of health care center 1 in advance (before the at-home patient receives actual service of health care center 1). As the basic data, the age, sex, height, weight, body fat ratio, blood pressure, exercise level, sleep times, meal times, and amount of food consumed are transmitted from at-home patient 2 to health care center 1. The further addition of genetic information derived from a DNA analysis as basic data of the at-home patient can both improve the reliability of the service and increase the scope of the service.

These basic data are normally dealt with in a single transmission (input), but it is also possible to resubmit in the event of changes, alternations, or additions either periodically or as circumstances dictate. In addition, testing companies may provide the service of measuring test items that are unfeasible in the home. For example, the test company may carry out precise tests of a morbidity by performing DNA analysis or special tests for hormones and antibodies present in test samples of urine or blood. When this service is chosen, relevant business 5 sends materials in advance such as containers for collecting samples or for transporting the samples.

Urine glucose values, measurement day and time, the total cumulative time a sensor has been used, the total cumulative number of times the sensor has been used, and calibration values are sent as the urine glucose data from at-home patient 2 to health care center 1.

Of these data, the total cumulative time of use of the biosensor and the total cumulative number of times of use of the biosensor are measured by a timer and counter incorporated in the urine glucose biosensor with each use thereof and then stored in a memory in the information processor 23. The urine glucose biosensor deteriorates depending on the number of times of use, due to chemical reaction with urine. For this reason, the biosensor is immerses into a standard solution from time to time to calibrate the urine glucose biosensor, and the calibration value is automatically registered in information processor 23. The last calibration value is transmitted from at-home patient 2 to health care center 1.

Of the data that are transmitted to health care center 1, basic data are registered in the database as the basic health care data. The urine glucose values of the urine glucose data, after being calibrated by the calibration value, are processed together with the measurement day and time to produce an easily recognizable format (a format that allows easy discernment of the diabetic morbidity). These results are both stored in the database and transmitted to the Internet designating the at-home patient as the transmission destination. These processed data serve as the basic service for the at-home patient. Of the urine glucose data, the cumulative time of use of the biosensor and the cumulative number of times of use of the biosensor are further totalized in health care center 1 to check the state of the biosensor and used for maintenance service S5.

When at-home patient 2 chooses any of comprehensive advice service S31, dietary treatment support service 32, exercise therapy support service S33, and medication support service S34 from the selective services S2, the processed urine glucose data described above are reviewed by a doctor, pharmacist, dietician, or exercise therapist.

An embodiment is shown in FIG. 6 in which specialist 4 is independent of health care center 1. In this type of embodiment, the specialist is affiliated in affairs with health care center 1 as a cooperating specialist and constitutes a site on the Internet linked with health care center 1. In this case, the processed urine glucose data described above are transmitted from health care center 1 to Internet 3 designating specialist 4 as the transmission destination. In some cases, however, a full-time specialist (a staff specialist) and a cooperating specialist may both belong to health care center 1. In such cases, health care center 1 requests service from a cooperating specialist by way of the Internet for services that a full-time specialist is not able to accommodate.

In order to provide dietary treatment support service S32, maintenance service S5, and insurance premium reduction support service S7, health care center 1 cooperates with food suppliers, urine glucose biosensor manufacturers, and life insurance providers and is also linked to these entities on the Internet.

If the at-home patient so desires, health care center 1 transmits the processed urine glucose data on Internet 3 designating the relevant business (life insurance provider) 5 as the transmission destination for the purpose of reducing a life insurance premium. In addition, health care center 1 transmits the results of a sensor state check on Internet 3 designating relevant business (urine glucose biosensor manufacturer) 5 as the transmission destination for the purpose of maintaining the urine glucose biosensor.

In response to the flow of data shown in FIG. 6, health care service flows as shown by the arrows in FIG. 7. In FIG. 7, the thick arrows represent the flow of articles, and the other arrows represent the flow of information.

As the services that an at-home patient receives, the figure shows: basic service, medication advice, dietary advice, exercise advice, judgment of a morbidity and comprehensive advice, mailing list service, food supply service, maintenance support service (component exchange service and consumable supply service), and insurance premium reduction support service; all of these services except the basic service being selective services.

Of these services, the basic service, medication advice, dietary advice, exercise advice, judgments of morbidity, and mailing list service are all information services and are provided from the health care center 1. The food supply service, component exchange service, consumable supply service, and insurance premium reduction support service (issue of an insurance contract) are services for articles and are provided to the at-home patient 2 from relevant business 5 by way of home delivery service 6.

The arrow issuing from specialist 4 in FIG. 7 represents the flow of two types of service. The first service is the provision of the specialized knowledge of specialists to health care center 1. The second service is the downloading of the service of specialist 4 directly to at-home patient 2. Since specialist 4 is linked to health care center 1 over the Internet, at-home patient 2 can read the page of health care center 1 on the display screen of information processor 23 at home and then access the page of specialist 4 by clicking on link characters or link images of the link-destination specialist on the display screen of this page.

The thin arrows from relevant business 5 represent a similar flow of service. At-home patient 2 can read the page of health care center 1 on the display screen of information processor 23 at home; access the page of relevant business 5 by clicking on link characters or link image of link-destination relevant business 5 on the display screen of this page; and thus obtain desired information by way of the Internet.

In the above-described embodiment, a urine glucose biosensor is used as the biosensor, and the mobidity that is the object of health care is diabetes.

However, the present invention can be applied to cases in which the biosensor is used to detect chemical substance other than a urine glucose. As mentioned hereinabove, testing device 101 of FIG. 1 can also measure the following items depending on the morbidity that is the object of health care by exchanging biosensor 103.

Morbidity: Diabetes
Measurement items: Glucose, ketone bodies, hydroxybutyric acid, C peptides, and other chemical substances that change according to the diabetic state.

Morbidity: Renal Disease
Measurement items: Protein, albumin, creatinine, oxalic acid, and other chemical substances that change according to the state of the renal disease.

Morbidity: Liver Disease
Measurement items: Bile acid, pyruvic acid, urobilinogen, bilirubin, and other chemical substances that change according to the state of the liver disease.

In addition, measurement items may include: lactic acid, which changes depending on the amount of exercise; and pH, which changes depending on diet.

By combining and analyzing these data, a criterion for the degree of stress or fatigue can be realized even in cases in which there is no particular medical problem.

As yet another service, it is possible to provide a service in which, when a home measurement device yields results that raise the suspicion of a disease or when a more detailed medical test is called for, a urine, blood, or DNA examination may be received at a special (clinical) test company.

As a service for the maintenance of materials necessary to home health care, trends in the frequency of use are analyzed based on maintenance data stored in the database to predict the time when the biosensor must be exchanged or the time when consumables are necessary.

By this analysis, it becomes feasible to make deliveries before there is a lack of any necessary articles, and further, determine monthly service charges and make charges according to the frequency of use.

The above-described health care service is a service for a registered at-home patient and in principle is provided for a charge. Charges for the service are made depending on the type of service. The cost of the service may in some cases be collected separately, or the cost of the service may be included in the cost of the device, or the cost of the service may include the cost of the device.

Health care center 1 may further establish a home page on the Internet and present information relevant to the activities of health care center 1 or offer services without charge.

It is to be understood, however, that although the characteristics and advantages of the present invention have been set forth in the foregoing description, the disclosure is illustrative only, and changes may be made in the arrangement of the parts within the scope of the appended claims.

What is claimed is:

1. A method of providing a home health care service, comprising steps of:
   providing access to a health care center on the Internet, said health care center having personal data necessary for the health care of registered at-home patients as basic health care data and also having the capability of inferring the health conditions of the at-home patients from measurement data provided by the at-home home patients and said basic health care data, and providing services necessary for health care or services appropriate to the inferred health conditions to said at-home patients;
   distributing biosensor devices to at-home patients who wish to receive a home health care service, said biosensor device having a capability of detecting predetermined chemical components contained in a substance discharged from a human body and automatically generating electrical measurement data at the position of discharge as occasion arises;
   collecting the measurement data of each registered at-home patient to said health care center from at-home patients by way of said Internet; and
   managing time-varying health conditions of the at-home patients over a period of time based on the collected measurement data as well as said basic health care data, and providing necessary services for maintaining the health of the at-home patients,
   wherein said biosensor device includes a urine testing device comprising:
   a urine collector for collecting urine inside a toilet bowl;
   a biosensor exchangeably attached inside said urine collector for detecting predetermined chemical component values contained in urine and converting said detected values into electrical signals;
   a support member for supporting said urine collector away from said toilet bowl during collection and also supporting a transmission path of said electrical signals, said support member being arranged so that said urine collector may be automatically or manually moved from a housing location to a prescribed use-position in the toilet bowl and vice versa; and
   a signal processor for processing electrical signals supplied from said biosensor through said transmission path.

2. The method of providing home health care service according to claim 1, comprising:
   measuring those components among the chemical components of urine that are associated with a morbidity and that change according to the daily health condition, over a period of time.

3. The method of providing a home health care service according to claim 2, wherein said health care center provides, as a basic service to all registered at-home patients, information that has been processed and arranged to enable an extraction of knowledge relating to a specific said morbidity; and provides, as selective services that can be selected by at-home patients, services that are appropriate to the inferred health conditions of said specific morbidity.

4. The method of providing a home health care service according to claim 2, wherein said method employs a biosensor for measuring glucose, ketone bodies, hydroxybutyric acid, C peptides, or other chemical components that relate to diabetes in cases in which the morbidity to be health-cared is diabetes.

5. The method of providing a home health care service according to claim 2, wherein said method employs a biosensor for measuring bile acid, pyruvic acid, urobilinogen, bilirubin, or other chemical components that relate to liver disease in cases in which the morbidity to be health-cared is a liver disease.

6. The method of providing a home health care service according to claim 2, wherein said method employs a biosensor for measuring protein, albumin, creatinine, oxalic acid, or other chemical components that relate to renal disease in cases in which the morbidity to be health-cared is a renal disease.

7. The method of providing a home health care service according to claim 2, wherein said method employs a biosensor for measuring lactic acid, the pH of urine, or other chemical components that serve as indicators of the degree of stress or fatigue in cases in which the morbidity to be health-cared is stress or fatigue.

8. A system for providing a home health care service, comprising:
a health care center on the Internet provided with a database for registering, as basic health care data, personal data necessary for the health care of registered at-home patients and for storing measurement data provided by at home patients as occasion arises over a period of time, said health care center having a function of inferring the health conditions of the at-home patients based on said measurement data as well as said basic health care data and providing services necessary for health care or services appropriate to the inferred health conditions, to the at-home patients; and
a service recipient device belonging to an at-home patient comprising: a biosensor for detecting predetermined chemical components that are contained in a substance discharged from said at-home patient and converting the detected values of said chemical components to electrical signals at the point of discharge when the discharge is conducted; a signal processor for processing an output of said biosensor and automatically generating measurement data as well as performing control of the communication between said service recipient device and said health care center and an information terminal for interfacing said signal processor and said Internet,
wherein said service recipient device delivers, under output control of said signal processor, measurement data that have been generated over a period of time together with time data that indicate the times when said biosensor detected said chemical component to said Internet, designating said health care center as the transmission destination; and said service recipient device receives, under input control of said signal processor, information transmitted from said health care center by way of said Internet,
wherein said health care center, when judging the transmission source of received measurement data being a service recipient device belonging to a registered at-home patient, stores the measurement data to said data base, and as demand arises, said health care center infers the health condition of the at-home patient based on stored measurement data and with reference to the registered basic health care data and provides information necessary for health care or services appropriate for the inferred health condition, to the at-home patient, and
wherein said biosensor device includes a urine testing device comprising:
a urine collector for collecting urine inside a toilet bowl;
a biosensor exchangeably attached inside said urine collector for detecting predetermined chemical component values contained in urine and converting said detected values into electrical signals;
a support member for supporting said urine collector away from said toilet bowl during collection and also supporting a transmission path of said electrical signals, said support member being arranged so that said urine collector may be automatically or manually moved from a housing location to a prescribed use-position in the toilet bowl and vice versa; and
a signal processor for processing electrical signals supplied from said biosensor through said transmission path.

9. The system for providing a home health care service according to claim 8, wherein:
said biosensor, arranged inside a toilet at the time of operation, detects those measurement components among the chemical components of urine that relate to a morbidity and that change according to a daily health condition, and converts the detected values to electrical signals; and
said signal processor is arranged outside of said toilet, processes electrical signals generated by said biosensor, and generates measurement data.

10. The system for providing a home health care service according to claim 8, wherein said health care center includes an expert system for inferring the health condition of an at-home patient based on measurement data provided by the at-home patient and said basic health care data registered in a database, and, when the possibility of a disease of the at-home patient is inferred, said health care center searches for optimum advice for the disease through said expert system.

11. The system for providing a home health care service according to claim 9, wherein said health care center has full-time specialists as staffs, or specialists linked to the health care center over the Internet, who diagnose the health condition of the at-home patient based on measurement data provided by at-home patient and said basic health care data to provide health care support for the at-home patient.

12. The system for providing a home health care service according to claim 11, wherein said health care center has full-time specialists as staff, or specialists linked with the health care center on the Internet, who provide support to the at-home patient regarding dietary treatment, exercise therapy, or medication, as a service appropriate to an inferred health condition.

13. The system for providing a home health care service according to claim 12, wherein a food supplier is linked to the health care center on the Internet, the food supplier configured to provide food planned by said health care center to at-home patients for implementing dietary treatment appropriate for an inferred health condition.

14. The system for providing home health care service according to claim 12, wherein said health care center provides, as a basic service to all registered at-home patients, measurement data that have been organized and processed so as to allow comprehension of information relating to a specific morbidity associated with chemical components that have been measured by said biosensor; and further provides, as a selective service that can be selected by at-home patients, support provided by said specialists for said specific morbidity.

15. The system for providing a home health care service according to claim 14, wherein as said selective service, a precise examination for a morbidity that has been inferred from measurement data is performed at home using instructional information and materials that have been sent beforehand.

16. The system for providing a home health care service according to claim 15, wherein said health care center has a business-affiliation with a testing company having a function of testing a morbidity of at-home patients, and, as a selective service, provides the testing company with basic health care data and measurement data of an at-home patient and has the testing company perform prescribed tests of the morbidity.

17. The system for providing a home health care service according to claim 9, wherein said morbidity is diabetes, and said biosensor is a sensor capable of measuring glucose, ketone bodies, hydroxybutyric acid, C peptides, or other chemical components that relate to diabetes.

18. The system for providing a home health care service according to claim 9, wherein said morbidity is a liver disease, and said biosensor is a sensor capable of measuring bile acid, pyruvic acid, urobilinogen, bilintbin, or other chemical components that relate to liver diseases.

19. The system for providing a home health care service according to claim 9, wherein said morbidity is a renal disease, and said biosensor is a sensor capable of measuring protein, albumin, creatinine, oxalic acid, or other chemical components that relate to renal diseases.

20. The system for providing a home health care service according to claim 9, wherein said biosensor is a sensor capable of measuring lactic acid, the pH of urine, or other chemical components that serve as indicators of the degree of stress or fatigue.

21. The system for providing a home health care service according to claim 8, wherein:
   said service recipient device has the functions of measuring the number of times the biosensor has been used, the cumulative amount of time the biosensor has been used and a calibration value of the biosensor and sending these measurement values to said health care center as biosensor maintenance data; and
   said health care center, as a biosensor maintenance service, stores said maintenance data in a database, notifies the at-home patient of the current biosensor state, and gives advance notice of the life of the biosensor to the at-home patient, based on the maintenance data stored in said database.

* * * * *